US010042156B2

(12) United States Patent
St. George

(10) Patent No.: US 10,042,156 B2
(45) Date of Patent: *Aug. 7, 2018

(54) ILLUMINATION BALANCING AND SOLID STATE NARROW BAND IMAGING UTILIZING FIBER BUNDLE DESIGN AND ASSEMBLY TECHNIQUES IN ENDOSCOPES

(71) Applicant: Gyrus ACMI, Inc., Southborough, MA (US)

(72) Inventor: Lawrence J. St. George, Sudbury, MA (US)

(73) Assignee: Gyrus ACMI, Inc., Southbourough, MA (US)

(*) Notice: Subject to any disclaimer, the term of this patent is extended or adjusted under 35 U.S.C. 154(b) by 73 days.

This patent is subject to a terminal disclaimer.

(21) Appl. No.: 15/389,597

(22) Filed: Dec. 23, 2016

(65) Prior Publication Data
US 2017/0108690 A1    Apr. 20, 2017

Related U.S. Application Data

(63) Continuation of application No. 14/710,950, filed on May 13, 2015, now Pat. No. 9,528,664.
(Continued)

(51) Int. Cl.
*D03D 15/00* (2006.01)
*G02B 23/24* (2006.01)
(Continued)

(52) U.S. Cl.
CPC ........ *G02B 23/2469* (2013.01); *A61B 1/0638* (2013.01); *A61B 1/0684* (2013.01);
(Continued)

(58) Field of Classification Search
CPC .......... G02B 6/0008; G02B 6/04; A61B 1/00; A61B 1/0661; A61B 1/0669
(Continued)

(56) References Cited

U.S. PATENT DOCUMENTS 3,889,662 A    6/1975   Mitsui
9,528,664 B2 * 12/2016  St. George ......... A61B 1/00167
(Continued)

FOREIGN PATENT DOCUMENTS

CN   101189540 A   5/2008
CN   103189780 A   7/2013
(Continued)

OTHER PUBLICATIONS

International Search Report; PCT/US2015/030502, dated Jul. 23, 2015, pp. 4.
(Continued)

*Primary Examiner* — Elmito Breval
*Assistant Examiner* — Meghan Ulanday
(74) *Attorney, Agent, or Firm* — Chapin IP Law, LLC

(57) ABSTRACT

A semiconductor-based light source device for an endoscope that provides for an even power distribution and/or color distribution of light. The semiconductor-based light source device includes a plurality of semiconductor light sources and a plurality of fiber bundles, in which the respective fiber bundles are each segregated into a plurality of fiber sub-bundles for directing substantially the same amount of illumination from a respective semiconductor light source to each of a corresponding plurality of illumination windows disposed at a distal end of the endoscope. By providing such a semiconductor-based light source device, in which the respective semiconductor light sources are operative to adjust the intensity and/or color or wavelength of the light emitted by the respective semiconductor light sources, a desired color temperature and/or color balance for illumination of tissue and/or other matter under examination by the endoscope can be achieved.

19 Claims, 5 Drawing Sheets

Related U.S. Application Data

(60) Provisional application No. 62/007,506, filed on Jun. 4, 2014.

(51) Int. Cl.
*A61B 1/06* (2006.01)
*A61B 1/07* (2006.01)
*F21V 8/00* (2006.01)
*G02B 6/04* (2006.01)
*A61B 1/00* (2006.01)

(52) U.S. Cl.
CPC .............. *A61B 1/07* (2013.01); *G02B 6/0006* (2013.01); *G02B 6/0008* (2013.01); *G02B 6/04* (2013.01); *A61B 1/00167* (2013.01)

(58) Field of Classification Search
USPC ........ 362/551, 554, 556; 600/101, 160, 165, 600/178, 182
See application file for complete search history.

(56) References Cited

U.S. PATENT DOCUMENTS

| | | |
|---|---|---|
| 2004/0241752 A1 | 12/2004 | Anderson et al. |
| 2012/0245421 A1 | 9/2012 | Kitano |
| 2013/0228707 A1 | 9/2013 | Nieminen |
| 2013/0267782 A1 | 10/2013 | Wieters et al. |

FOREIGN PATENT DOCUMENTS

| | | |
|---|---|---|
| EP | 1 051 687 A1 | 11/2000 |
| EP | 1 809 173 A1 | 2/2008 |

OTHER PUBLICATIONS

Office Action by the State Intellectual Property Office of China, Application No: 201580040315.1, dated Dec. 4, 2017, pp. 6.

* cited by examiner

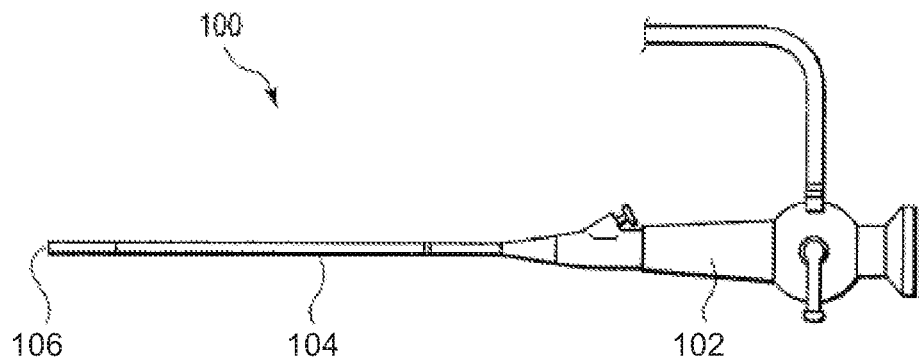
FIG. 1a – Prior art
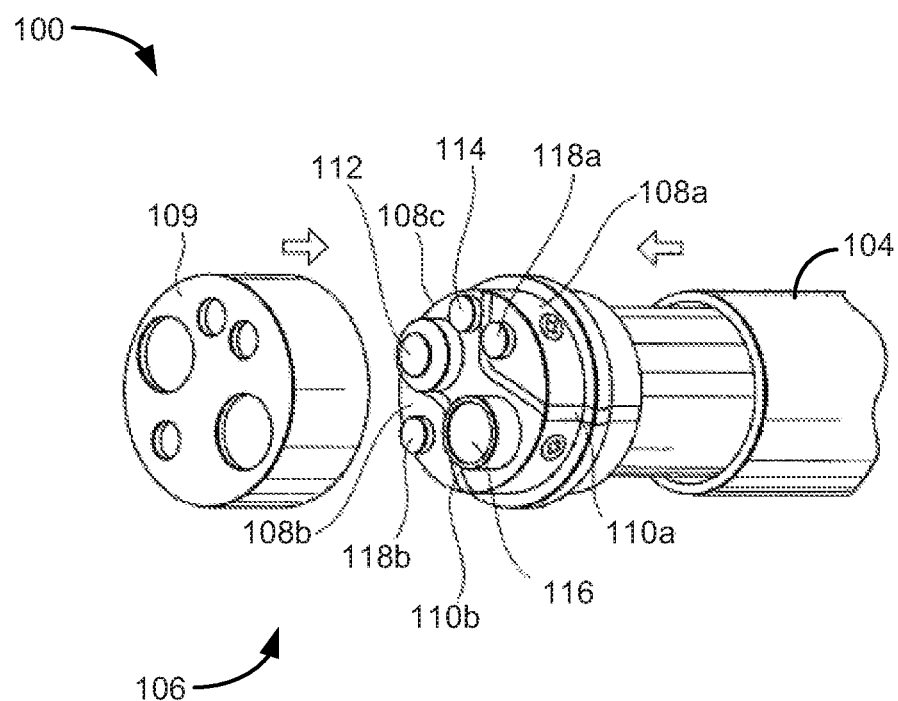
FIG. 1b – Prior art

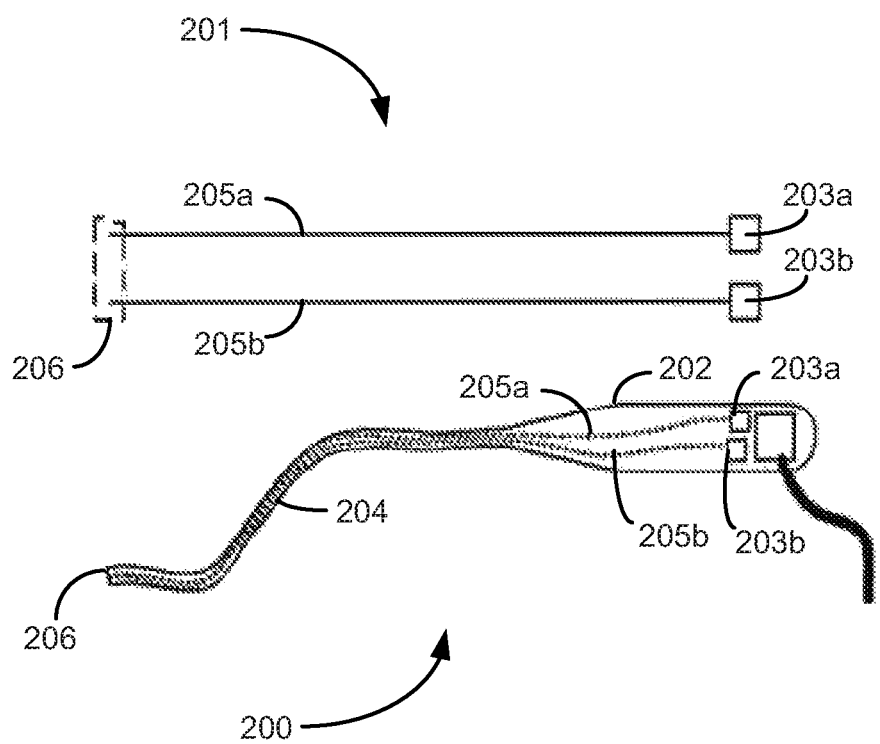
FIG. 2 – Prior art

ILLUMINATION BALANCING AND SOLID STATE NARROW BAND IMAGING UTILIZING FIBER BUNDLE DESIGN AND ASSEMBLY TECHNIQUES IN ENDOSCOPES

CROSS-REFERENCE TO RELATED APPLICATIONS

This application is a continuation of prior U.S. patent application Ser. No. 14/710,950 filed May 13, 2015 entitled ILLUMINATION BALANCING AND SOLID STATE NARROW BAND IMAGING UTILIZING FIBER BUNDLE DESIGN AND ASSEMBLY TECHNIQUES IN ENDOSCOPES, which claims benefit of the priority of U.S. Provisional Patent Application Ser. No. 62/007,506 filed Jun. 4, 2014 entitled ILLUMINATION BALANCING AND SOLID STATE NARROW BAND IMAGING UTILIZING FIBER BUNDLE DESIGN AND ASSEMBLY TECHNIQUES IN ENDOSCOPES.

TECHNICAL FIELD

The present application relates generally to light source devices, and more specifically to a semiconductor-based light source device for an endoscope apparatus that provides for a more even power distribution and/or color distribution of light, and allows for use of targeted wavelengths to enhance visibility of features of interest.

BACKGROUND

Endoscopes are known that employ semiconductor light sources for illuminating the interior of hollow organs and/or cavities within the human body. For example, such endoscopes may be employed to examine the interior of a small intestine in an enteroscopy procedure, a large intestine in a colonoscopy procedure, an upper respiratory tract in a rhinoscopy procedure, a lower respiratory tract in a bronchoscopy procedure, etc. A conventional endoscope apparatus can include two separate fiber bundles, and two semiconductor light sources such as light-emitting diodes (LEDs) coupled, at a proximal end of the endoscope apparatus, to the two separate fiber bundles, respectively, thereby providing two separate illuminations at a distal end of the endoscope apparatus for illuminating the interior of a small intestine, a large intestine, an upper respiratory tract, a lower respiratory tract, etc., during the performance of a respective medical examination procedure.

The conventional endoscope apparatus discussed above can have drawbacks, however, in that the two separate illuminations provided at the distal end of the endoscope apparatus can cause uneven lighting and/or unintended coloring of tissue and/or other matter under examination by the endoscope apparatus, due to the two LEDs providing the respective illuminations possibly being not well-matched in power output and/or color output. To provide for a more even lighting while avoiding unintended coloring of such tissue and/or other matter under examination by the endoscope apparatus, some processes of manufacturing endoscopes have included additional testing of LEDs to assure that the LEDs selected for use in each endoscope apparatus are well-matched in power output and/or color output over specified ranges of operation. However, such additional testing of LEDs during the endoscope manufacturing process can undesirably increase the final cost of the endoscopes.

It would therefore be desirable to have semiconductor-based light source devices for endoscopes that avoid at least some of the drawbacks found in conventional endoscope apparatuses, such as those discussed above.

SUMMARY

In accordance with the present application, a semiconductor-based light source device for an endoscope apparatus, or any other suitable apparatus, is disclosed that provides for a more even power distribution and/or color distribution of light with ease of implementation. The semiconductor-based light source device can be employed in conjunction with an endoscope apparatus that has a distal end, and at least a first illumination window and a second illumination window disposed at the distal end of the endoscope apparatus.

In one aspect, the semiconductor-based light source device can include a first semiconductor light source, a second semiconductor light source, a first fiber bundle, and a second fiber bundle. The first fiber bundle includes a first plurality of optical fibers segregated to form at least a first fiber sub-bundle and a second fiber sub-bundle. Similarly, the second fiber bundle includes a second plurality of optical fibers segregated to form at least a third fiber sub-bundle and a fourth fiber sub-bundle. The first fiber sub-bundle, the second fiber sub-bundle, the third fiber sub-bundle, and the fourth fiber sub-bundle each have a distal end and a proximal end. The proximal end of each of the first fiber sub-bundle and the second fiber sub-bundle is configured to receive light emitted by the first semiconductor light source, and the proximal end of each of the third fiber sub-bundle and the fourth fiber sub-bundle is configured to receive light emitted by the second semiconductor light source. The distal end of the first fiber sub-bundle and the distal end the second fiber sub-bundle are operative to direct the light emitted by the first semiconductor light source through the first illumination window and the second illumination window, respectively, at the distal end of the endoscope apparatus. Likewise, the distal end of the third fiber sub-bundle and the distal end of the fourth fiber sub-bundle are operative to direct the light emitted by the second semiconductor light source through the first illumination window and the second illumination window, respectively, at the distal end of the endoscope apparatus.

In an exemplary aspect, the first semiconductor light source and the second semiconductor light source can emit light having the same color or wavelength or different colors or wavelengths. In a further exemplary aspect, one or more of the first semiconductor light source and the second semiconductor light source can emit light in a selected color or wavelength band. In another exemplary aspect, the first semiconductor light source can emit light having a broad wavelength bandwidth (e.g., white light), and the second semiconductor light source can emit light having a narrow wavelength bandwidth. In still another exemplary aspect, one or more of the first semiconductor light source and the second semiconductor light source can emit light having a selectable and/or adjustable intensity and/or color or wavelength. In yet another exemplary aspect, each of the first fiber sub-bundle, the second fiber sub-bundle, the third fiber sub-bundle, and the fourth fiber sub-bundle can include at least approximately the same number of optical fibers.

In a further aspect, the semiconductor-based light source device can include at least a first semiconductor light source, a second semiconductor light source, a third semiconductor light source, and a fourth semiconductor light source. The semiconductor-based light source device can further include at least a first fiber bundle, a second fiber bundle, a third fiber bundle, and a fourth fiber bundle. The first fiber bundle includes a first plurality of optical fibers segregated to form at least a first fiber sub-bundle and a second fiber sub-bundle, and the second fiber bundle includes a second plurality of optical fibers segregated to form at least a third fiber sub-bundle and a fourth fiber sub-bundle. Similarly, the third fiber bundle includes a third plurality of optical fibers segregated to form at least a fifth fiber sub-bundle and a sixth fiber sub-bundle, and the fourth fiber bundle includes a fourth plurality of optical fibers segregated to form at least a seventh fiber sub-bundle and an eighth fiber sub-bundle.

The first fiber sub-bundle, the second fiber sub-bundle, the third fiber sub-bundle, the fourth fiber sub-bundle, the fifth fiber sub-bundle, the sixth fiber sub-bundle, the seventh fiber sub-bundle, and the eighth fiber sub-bundle each have a distal end and a proximal end. The proximal end of each of the first fiber sub-bundle and the second fiber sub-bundle is configured to receive light emitted by the first semiconductor light source, and the proximal end of each of the third fiber sub-bundle and the fourth fiber sub-bundle is configured to receive light emitted by the second semiconductor light source. The proximal end of each of the fifth fiber sub-bundle and the sixth fiber sub-bundle is configured to receive light emitted by the third semiconductor light source, and the proximal end of each of the seventh fiber sub-bundle and the eighth fiber sub-bundle is configured to receive light emitted by the fourth semiconductor light source.

The distal end of the first fiber sub-bundle and the distal end of the second fiber sub-bundle are operative to direct the light emitted by the first semiconductor light source through the first illumination window and the second illumination window, respectively, at the distal end of the endoscope apparatus. The distal end of the third fiber sub-bundle and the distal end of the fourth fiber sub-bundle are operative to direct the light emitted by the second semiconductor light source through the first illumination window and the second illumination window, respectively, at the distal end of the endoscope apparatus. Similarly, the distal end of the fifth fiber sub-bundle and the distal end the sixth fiber sub-bundle are operative to direct the light emitted by the third semiconductor light source through the first illumination window and the second illumination window, respectively, at the distal end of the endoscope apparatus. The distal end of the seventh fiber sub-bundle and the distal end of the eighth fiber sub-bundle are operative to direct the light emitted by the fourth semiconductor light source through the first illumination window and the second illumination window, respectively, at the distal end of the endoscope apparatus.

In an exemplary aspect, the first semiconductor light source, the second semiconductor light source, and the third semiconductor light source can emit light having a red (R) color, a green (G) color, and a blue (B) color, respectively, such that a combination of RGB colored light collectively directed by the first fiber sub-bundle, the third fiber sub-bundle, and the fifth fiber sub-bundle through the first illumination window produces a white light, and a combination of the RGB colored light collectively directed by the second fiber sub-bundle, the fourth fiber sub-bundle, and the sixth fiber sub-bundle through the second illumination window likewise produces a white light. In this exemplary aspect, the fourth semiconductor light source can be configured to emit light having a selected color or wavelength bandwidth, such as a selected narrow wavelength bandwidth. In a further exemplary aspect, one or more of the first semiconductor light source, the second semiconductor light source, the third semiconductor light source, and the fourth semiconductor light source are operative to select and/or adjust the intensity and/or color or wavelength of the light emitted by the respective semiconductor light sources. In another exemplary aspect, each of the first fiber sub-bundle, the second fiber sub-bundle, the third fiber sub-bundle, the fourth fiber sub-bundle, the fifth fiber sub-bundle, the sixth fiber sub-bundle, the seventh fiber sub-bundle, and the eighth fiber sub-bundle can include at least approximately the same number of optical fibers.

By providing a semiconductor-based light source device for an endoscope apparatus, or any other suitable apparatus, that includes a plurality of semiconductor light sources and a plurality of fiber bundles, in which the respective fiber bundles are each segregated into a plurality of fiber sub-bundles for directing substantially the same amount of illumination from a respective semiconductor light source to each of a corresponding plurality of illumination windows disposed at a distal end of the endoscope apparatus, a more even power distribution and/or color distribution of light at the distal end of the endoscope apparatus can be achieved with ease of implementation. Further, by providing such a semiconductor-based light source device in which one or more of the respective semiconductor light sources are operative to select and/or adjust the intensity and/or color or wavelength of the light emitted by the respective semiconductor light sources, a desired color temperature and/or color balance for illumination of tissue and/or other matter under examination by the endoscope apparatus can be further achieved.

Other features, functions, and aspects of the invention will be evident from the Drawings and/or the Detailed Description of the Invention that follow.

BRIEF DESCRIPTION OF THE DRAWINGS

The invention will be more fully understood with reference to the following Detailed Description of the Invention in conjunction with the drawings of which:

FIG. 1a is a side view of a conventional endoscope apparatus;

FIG. 1b is a perspective view of a distal end of the conventional endoscope apparatus of FIG. 1a;

FIG. 2 is a plan view of a conventional semiconductor-based light source device for the conventional endoscope apparatus of FIGS. 1a and 1b;

DETAILED DESCRIPTION

Figure 3:
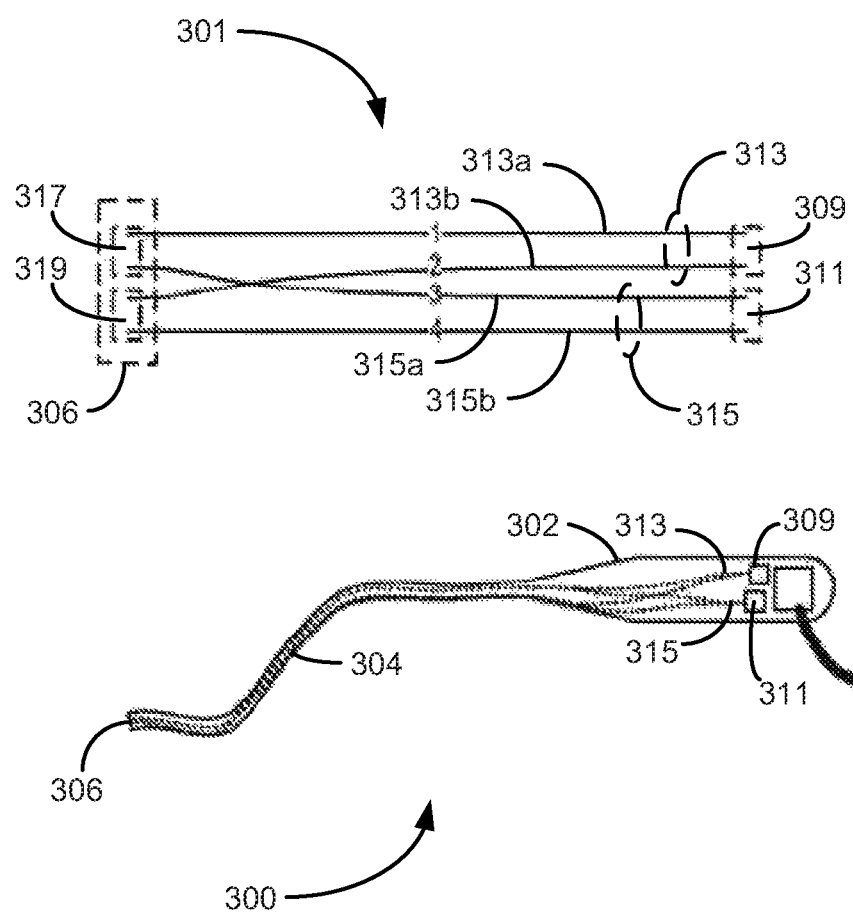
FIG. 3 is a plan view of an exemplary semiconductor-based light source device for an exemplary endoscope apparatus, in accordance with the present application.

The disclosures of U.S. patent application Ser. No. 14/710,950 filed May 13, 2015 entitled ILLUMINATION BALANCING AND SOLID STATE NARROW BAND IMAGING UTILIZING FIBER BUNDLE DESIGN AND ASSEMBLY TECHNIQUES IN ENDOSCOPES, and U.S.

Provisional Patent Application Ser. No. 62/007,506 filed Jun. 4, 2014 entitled ILLUMINATION BALANCING AND SOLID STATE NARROW BAND IMAGING UTILIZING FIBER BUNDLE DESIGN AND ASSEMBLY TECHNIQUES IN ENDOSCOPES, are hereby incorporated herein by reference in their entirety.

A semiconductor-based light source device for an endoscope apparatus, or any other suitable apparatus, is disclosed that provides for a more even power distribution and/or color distribution of light with ease of implementation. The disclosed semiconductor-based light source device includes a plurality of semiconductor light sources and a plurality of fiber bundles, in which the respective fiber bundles are each segregated into a plurality of fiber sub-bundles for directing substantially the same amount of illumination from a respective semiconductor light source to each of a corresponding plurality of illumination windows disposed at a distal end of the endoscope apparatus. By providing such a semiconductor-based light source device, in which one or more of the respective semiconductor light sources are operative to select and/or adjust the intensity and/or color or wavelength of the light emitted by the respective semiconductor light sources, a desired color temperature and/or color balance for illumination of tissue and/or other matter under examination by the endoscope apparatus can be achieved.

FIG. 1a depicts a conventional endoscope apparatus 100, which can include a control unit 102, an elongated insertion portion 104 extending from the control unit 102, and an end portion 106 located at a distal end of the endoscope apparatus 100. During a medical examination procedure, a health care professional typically inserts the elongated insertion portion 104 of the endoscope apparatus 100 into a hollow organ or cavity within the body of his or her patient, and positions the end portion 106 of the endoscope apparatus 100 near target tissue and/or other matter for subsequent examination thereof.

FIG. 1b depicts a detailed, partially exploded view of the end portion 106 at the distal end of the conventional endoscope apparatus 100 (see also FIG. 1a). As shown in FIG. 1b, the end portion 106 includes three end sections 108a, 108b, 108c arranged in a substantially interlocking relationship, and a cover portion 109 configured to cover the respective end sections 108a, 108b, 108c. The two end portions 108a, 108c are coupled to one another through a heat-insulating material 110a, and the two end portions 108b, 108c are likewise coupled to one another through a heat-insulating material 110b. The end portion 108c includes a solid-state image sensor 112, an air/water supply nozzle 114, and a suction channel 116. The end portion 108a includes a first illumination window 118a, and the end portion 108b includes a second illumination window 118b.

FIG. 2 depicts a conventional endoscope apparatus 200, as well as a plan view of a conventional semiconductor-based light source device 201 that can be incorporated into the endoscope apparatus 200. For example, the conventional endoscope apparatus 200 can be configured like the conventional endoscope apparatus 100 of FIGS. 1a and 1b. As shown in FIG. 2, the endoscope apparatus 200 includes a control unit 202, an elongated insertion portion 204 extending from the control unit 202, and an end portion 206 located at a distal end of the endoscope apparatus 200.

As further shown in FIG. 2, the conventional semiconductor-based light source device 201 includes a first semiconductor light source 203a, a second semiconductor light source 203b, a first fiber bundle 205a, and a second fiber bundle 205b. The first fiber bundle 205a includes a first plurality of optical fibers, and the second fiber bundle 205b includes a second plurality of optical fibers. The first fiber bundle 205a and the second fiber bundle 205b each have a distal end and a proximal end. The proximal end of the first fiber bundle 205a is configured to receive light emitted by the first semiconductor light source 203a, and the proximal end of the second fiber bundle 205b is configured to receive light emitted by the second semiconductor light source 203b.

The distal end of the first fiber bundle 205a is operative to direct the light emitted by the first semiconductor light source 203a through a first illumination window (such as the illumination window 118a; see FIG. 1b), which is included in the end portion 206 at the distal end of the conventional endoscope apparatus 200. Similarly, the distal end of the second fiber bundle 205b is operative to direct the light emitted by the second semiconductor light source 203b through a second illumination window (such as the illumination window 118b; see FIG. 1b), which is also included in the end portion 206 at the distal end of the endoscope apparatus 200. Because the first semiconductor light source 203a and the second semiconductor light source 203b may not be well-matched in power output and/or color output, the two separate illuminations provided at the distal end of the endoscope apparatus 200 can cause uneven lighting and/or unintended coloring of tissue and/or other matter under examination by the endoscope apparatus 200, during the performance of a specific medical examination procedure.

FIG. 3 depicts an illustrative embodiment of an exemplary endoscope apparatus 300, as well as a plan view of a semiconductor-based light source device 301 that can be incorporated into the endoscope apparatus 300, in accordance with the present application. As shown in FIG. 3, the endoscope apparatus 300 includes a control unit 302, an elongated insertion portion 304 extending from the control unit 302, and an end portion 306 located at a distal end of the endoscope apparatus 300. As further shown in FIG. 3, the semiconductor-based light source device 301 includes a first semiconductor light source 309, a second semiconductor light source 311, at least a first fiber bundle 313, and at least a second fiber bundle 315.

As further shown in FIG. 3, the first fiber bundle 313 includes a first plurality of optical fibers segregated to form at least a first fiber sub-bundle 313a and a second fiber sub-bundle 313b. Similarly, the second fiber bundle 315 includes a second plurality of optical fibers segregated to form at least a third fiber sub-bundle 315a and a fourth fiber sub-bundle 315b. The first fiber sub-bundle 313a, the second fiber sub-bundle 313b, the third fiber sub-bundle 315a, and the fourth fiber sub-bundle 315b each have a distal end and a proximal end. The proximal end of each of the first fiber sub-bundle 313a and the second fiber sub-bundle 313b is configured to receive light emitted by the first semiconductor light source 309, and the proximal end of each of the third fiber sub-bundle 315a and the fourth fiber sub-bundle 315b is configured to receive light emitted by the second semiconductor light source 311.

The distal end of the first fiber sub-bundle 313a and the distal end the second fiber sub-bundle 313b are operative to direct the light emitted by the first semiconductor light source 309 through a first illumination window 317 and a second illumination window 319, respectively, both of which are included in the end portion 306 at the distal end of the endoscope apparatus 300. Likewise, the distal end of the third fiber sub-bundle 315a and the distal end of the fourth fiber sub-bundle 315b are operative to direct the light emitted by the second semiconductor light source 311 through the first illumination window 317 and the second illumination window 319, respectively, at the distal end of the endoscope apparatus 300.

For example, the first semiconductor light source 309 and the second semiconductor light source 311 can each be implemented as a light-emitting diode (LED), a laser diode, or any other suitable semiconductor light source. Further, the first semiconductor light source 309 and the second semiconductor light source 311 can each be configured to emit light having the same color or wavelength or different colors or wavelengths. One or more of the first semiconductor light source 309 and the second semiconductor light source 311 can also be configured to emit light in a selected color or wavelength band. For example, the first semiconductor light source 309 can be configured to emit light having a broad wavelength bandwidth (e.g., white light), while the second semiconductor light source 311 can be configured to emit light having a narrow wavelength bandwidth.

In addition, one or more of the first semiconductor light source 309 and the second semiconductor light source 311 can be configured to emit light having a selectable and/or adjustable intensity and/or color or wavelength. For example, such functionality of selecting and/or adjusting the intensity and/or color or wavelength of the respective semiconductor light sources can be provided at least in part by the control unit 302 included in the endoscope apparatus 300. Moreover, each of the first fiber sub-bundle 313a, the second fiber sub-bundle 313b, the third fiber sub-bundle 315a, and the fourth fiber sub-bundle 315b can include at least approximately the same number of optical fibers for directing substantially the same amount of illumination from each of the respective semiconductor light sources 309, 311 to each of the respective illumination windows 317, 319 at the distal end of the endoscope apparatus 300. In this way, uneven lighting and/or unintended coloring of tissue and/or other matter under examination by the endoscope apparatus 300, due to the respective semiconductor light sources 309, 311 possibly being not well-matched in power output and/or color output, can be avoided, during the performance of a specific medical examination procedure.

Figure 4A:
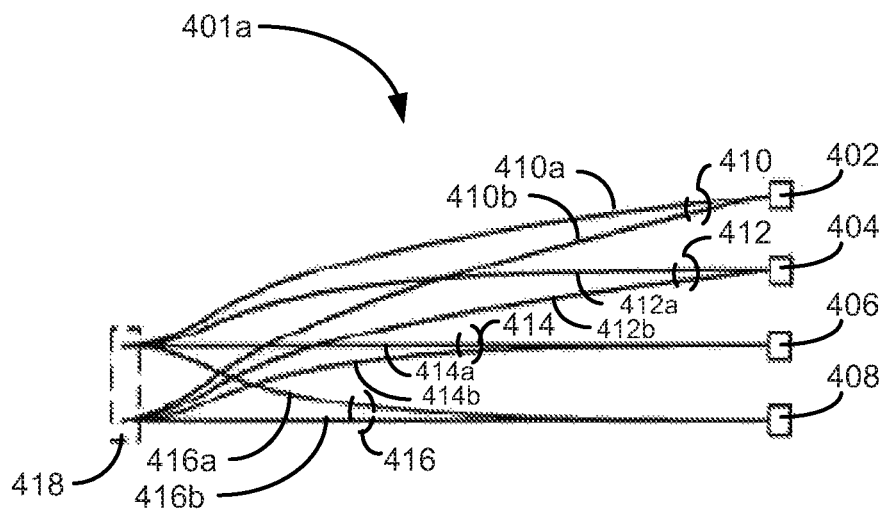
FIG. 4a is a plan view of an alternative exemplary embodiment of the semiconductor-based light source device of FIG. 3.

The disclosed semiconductor-based light source device for an endoscope apparatus will be further understood with reference to the following illustrative examples. In a first illustrative example (discussed herein with reference to FIG. 4a), an exemplary semiconductor-based light source device 401a for an endoscope apparatus (such as the endoscope apparatus 300; see FIG. 3) is provided, including a first semiconductor light source 402, a second semiconductor light source 404, a third semiconductor light source 406, and a fourth semiconductor light source 408. The semiconductor-based light source device 401a further includes a first fiber bundle 410, a second fiber bundle 412, a third fiber bundle 414, and a fourth fiber bundle 416. The first fiber bundle 410 includes a first plurality of optical fibers segregated to form at least a first fiber sub-bundle 410a and a second fiber sub-bundle 410b, and the second fiber bundle 412 includes a second plurality of optical fibers segregated to form at least a third fiber sub-bundle 412a and a fourth fiber sub-bundle 412b. Similarly, the third fiber bundle 414 includes a third plurality of optical fibers segregated to form at least a fifth fiber sub-bundle 414a and a sixth fiber sub-bundle 414b, and the fourth fiber bundle 416 includes a fourth plurality of optical fibers segregated to form at least a seventh fiber sub-bundle 416a and an eighth fiber sub-bundle 416b.

The first fiber sub-bundle 410a, the second fiber sub-bundle 410b, the third fiber sub-bundle 412a, the fourth fiber sub-bundle 412b, the fifth fiber sub-bundle 414a, the sixth fiber sub-bundle 414b, the seventh fiber sub-bundle 416a, and the eighth fiber sub-bundle 416b each have a distal end and a proximal end. The proximal end of each of the first fiber sub-bundle 410a and the second fiber sub-bundle 410b is configured to receive light emitted by the first semiconductor light source 402, and the proximal end of each of the third fiber sub-bundle 412a and the fourth fiber sub-bundle 412b is configured to receive light emitted by the second semiconductor light source 404. The proximal end of each of the fifth fiber sub-bundle 414a and the sixth fiber sub-bundle 414b is configured to receive light emitted by the third semiconductor light source 406, and the proximal end of each of the seventh fiber sub-bundle 416a and the eighth fiber sub-bundle 416b is configured to receive light emitted by the fourth semiconductor light source 408.

The distal end of the first fiber sub-bundle 410a and the distal end the second fiber sub-bundle 410b are operative to direct the light emitted by the first semiconductor light source 402 through a first illumination window (such as the illumination window 317; see FIG. 3) and a second illumination window (such as the illumination window 319; see FIG. 3), respectively, both of which are included in an end portion 418 at the distal end of the endoscope apparatus. The distal end of the third fiber sub-bundle 412a and the distal end of the fourth fiber sub-bundle 412b are likewise operative to direct the light emitted by the second semiconductor light source 404 through the first illumination window and the second illumination window, respectively, at the distal end of the endoscope apparatus. Similarly, the distal end of the fifth fiber sub-bundle 414a and the distal end the sixth fiber sub-bundle 414b are operative to direct the light emitted by the third semiconductor light source 406 through the first illumination window and the second illumination window, respectively, at the distal end of the endoscope apparatus. The distal end of the seventh fiber sub-bundle 416a and the distal end of the eighth fiber sub-bundle 416b are likewise operative to direct the light emitted by the fourth semiconductor light source 408 through the first illumination window and the second illumination window, respectively, at the distal end of the endoscope apparatus.

In this first illustrative example, one or both of the first semiconductor light source 402 and the second semiconductor light source 404 can be configured to emit light having a selected color or wavelength bandwidth, while one or both of the third semiconductor light source 406 and the fourth semiconductor light source 408 can be configured to emit light having a broad wavelength bandwidth (e.g., white light). For example, the first and second semiconductor light sources 402, 404 can be implemented as single color (e.g., red, green, blue, etc.) LEDs and/or laser diodes having an operative bandwidth in the selected range of interest, and the third and fourth semiconductor light sources 406, 408 can be implemented as white light-emitting diodes ("white LEDs"). In this way, the first and second semiconductor light sources 402, 404 emitting light having the selected color or wavelength bandwidth can provide illumination enhancement of tissue and/or other matter under examination by the endoscope apparatus, while the third and fourth semiconductor light sources 406, 408 provide broadband illumination of such tissue and/or other matter under examination by the endoscope apparatus.

It is noted that one or both of the third semiconductor light source 406 and the fourth semiconductor light source 408 can be configured to emit white light having a selectable and/or adjustable intensity, thereby allowing the level of broadband illumination to be varied, as desired and/or required, for effectively observing the tissue and/or other matter under examination by the endoscope apparatus. Likewise, one or both of the first semiconductor light source 402 and the second semiconductor light source 404 can be configured to emit light having the selected color or wavelength bandwidth with a selectable and/or adjustable intensity, thereby allowing the level of illumination enhancement to be varied, as desired and/or required, for more effectively observing such tissue and/or other matter under examination by the endoscope apparatus.

Figure 4B:
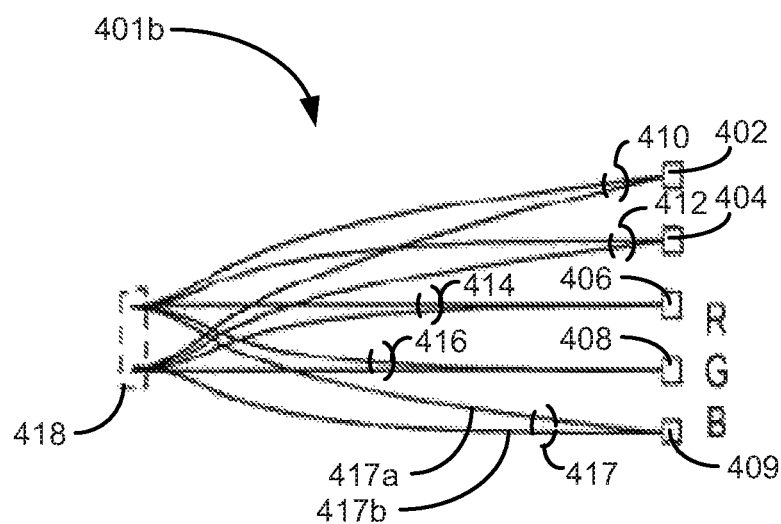
FIG. 4b is a plan view of a further alternative exemplary embodiment of the semiconductor-based light source device of FIG. 3.

In a second illustrative example (as discussed herein with reference to FIG. 4b), an exemplary semiconductor-based light source device 401b for an endoscope apparatus (such as the endoscope apparatus 300; see FIG. 3) is provided, including the first semiconductor light source 402, the second semiconductor light source 404, the third semiconductor light source 406, the fourth semiconductor light source 408, and the fifth semiconductor light source 409, as well as the first fiber bundle 410, the second fiber bundle 412, the third fiber bundle 414, the fourth fiber bundle 416, and the fifth fiber bundle 417. The semiconductor-based light source device 401b of FIG. 4b is like the semiconductor-based light source device 401a of FIG. 4a, with the exception of an additional fifth semiconductor light source 409 and an additional fifth fiber bundle 417.

The fifth fiber bundle 417 includes a fifth plurality of optical fibers segregated to form at least a ninth fiber sub-bundle 417a and a tenth fiber sub-bundle 417b. The ninth fiber sub-bundle 417a and the tenth fiber sub-bundle 417b each have a distal end and a proximal end. The proximal end of each of the ninth fiber sub-bundle 417a and the tenth fiber sub-bundle 417b is configured to receive light emitted by the fifth semiconductor light source 409. Further, the distal end of the ninth fiber sub-bundle 417a and the distal end the tenth fiber sub-bundle 417b are operative to direct the light emitted by the fifth semiconductor light source 409 through the first illumination window (such as the illumination window 317; see FIG. 3) and the second illumination window (such as the illumination window 319; see FIG. 3), respectively, both of which are included in the end portion 418 at the distal end of the endoscope apparatus.

In this second illustrative example, one or both of the first semiconductor light source 402 and the second semiconductor light source 404 can be configured to emit light having a selected color or wavelength bandwidth, such as a selected narrow wavelength bandwidth, for providing illumination enhancement of tissue and/or other matter under examination by the endoscope apparatus. Further, the third semiconductor light source 406, the fourth semiconductor light source 408, and the fifth semiconductor light source 409 can be configured to emit light having a red (R) color, a green (G) color, and a blue (B) color, respectively, such that a combination of RGB colored light collectively directed by the fifth fiber sub-bundle 414a, the seventh fiber sub-bundle 416a, and the ninth fiber sub-bundle 417a through the first illumination window produces a white light, and a combination of the RGB colored light collectively directed by the sixth fiber sub-bundle 414b, the eighth fiber sub-bundle 416b, and the tenth fiber sub-bundle 417b through the second illumination window likewise produces a white light, thereby providing broadband illumination of such tissue and/or other matter under examination by the endoscope apparatus.

It is noted that one or more of the third semiconductor light source 406, the fourth semiconductor light source 408, and the fifth semiconductor light source 409 can be configured to emit light having the red (R) color, the green (G) color, and the blue (B) color, respectively, with a selectable and/or adjustable intensity, thereby allowing the color temperature and/or color balance to be varied, as desired and/or required, for broadband illumination of the tissue and/or other matter under examination by the endoscope apparatus. Likewise, one or both of the first semiconductor light source 402 and the second semiconductor light source 404 can be configured to emit light having the selected color or wavelength bandwidth with a selectable and/or adjustable intensity, thereby allowing the level of specialized illumination to be varied, as desired and/or required, for illumination enhancement of the tissue and/or other matter under examination by the endoscope apparatus.

It is further noted that, in the first and second illustrative examples discussed above, each of the fiber sub-bundles included in the semiconductor-based light source devices 401a, 401b can include at least approximately the same number of optical fibers for directing substantially the same amount of illumination from each of the respective semiconductor light sources to each of the respective illumination windows at the distal end of the endoscope apparatus. In this way, the semiconductor-based light source devices 401a, 401b can provide for a more even lighting while avoiding unintended coloring of the tissue and/or other matter under examination by the endoscope apparatus, obviating the need for additional testing of the semiconductor light sources to assure that the respective semiconductor light sources are well-matched in power output and/or color output over their specified ranges of operation.

Having described the above exemplary embodiments of the disclosed semiconductor-based light source device for an endoscope apparatus, other alternative embodiments or variations may be made. For example, it was described herein that the respective fiber bundles included in the disclosed semiconductor-based light source device can each be segregated into a plurality of fiber sub-bundles, in which each fiber sub-bundle can include at least approximately the same number of optical fibers for directing substantially the same amount of illumination from each of the respective semiconductor light sources to each of the respective illumination windows located at the distal end of the endoscope apparatus. In an alternative embodiment, one or more of the respective fiber bundles included in the disclosed semiconductor-based light source device can be segregated into a first fiber sub-bundle and a second fiber sub-bundle. Further, a first number of optical fibers in both the first fiber sub-bundle and the second fiber sub-bundle can be employed to direct broadband illumination (e.g., white light) to each of the illumination windows at the distal end of the endoscope apparatus, while a different number (e.g., a smaller number) of optical fibers in both the first fiber sub-bundle and the second fiber sub-bundle can be employed to provide illumination enhancement (e.g., light having a selected narrow wavelength bandwidth) to each of the illumination windows at the distal end of the endoscope apparatus. In addition, one or more light-mixing rods (integrators) can be incorporated into the semiconductor-based light source device to provide for a more uniform broadband illumination and/or illumination enhancement at the distal end of the endoscope apparatus.

It is contemplated that each fiber bundle associated with each semiconductor light source may alternatively be provided with three or more fiber sub-bundles. It is contemplated that each fiber bundle associated with each semiconductor light source may alternatively be provided with an unequal number of fiber sub-bundles. It is contemplated that each fiber sub-bundle may alternatively be provided with an unequal number of fibers. For example, generally speaking, laser semiconductor light sources would not need as many fibers as LED semiconductor light sources, due to higher power and smaller beam size for laser semiconductor light sources.

It was also described herein that the functionality of selecting and/or adjusting the intensity and/or color or wavelength of the respective semiconductor light sources can be provided at least in part by the control unit (e.g., the control unit 302; see FIG. 3) included in the endoscope apparatus. In an alternative embodiment, the additional functionality of selecting and/or adjusting the power distributed to the respective semiconductor light sources can also be provided at least in part by the control unit included in the endoscope apparatus. For example, such a control unit can include at least one computerized processor or controller operative to execute at least one program out of at least one memory. Further, independent control over the selection and/or adjustment of the intensity, color or wavelength, and/or power associated with the respective semiconductor light sources can be achieved at least in part by suitably programming the computerized processor/controller and memory for performing the desired functionality.

Figure 5:
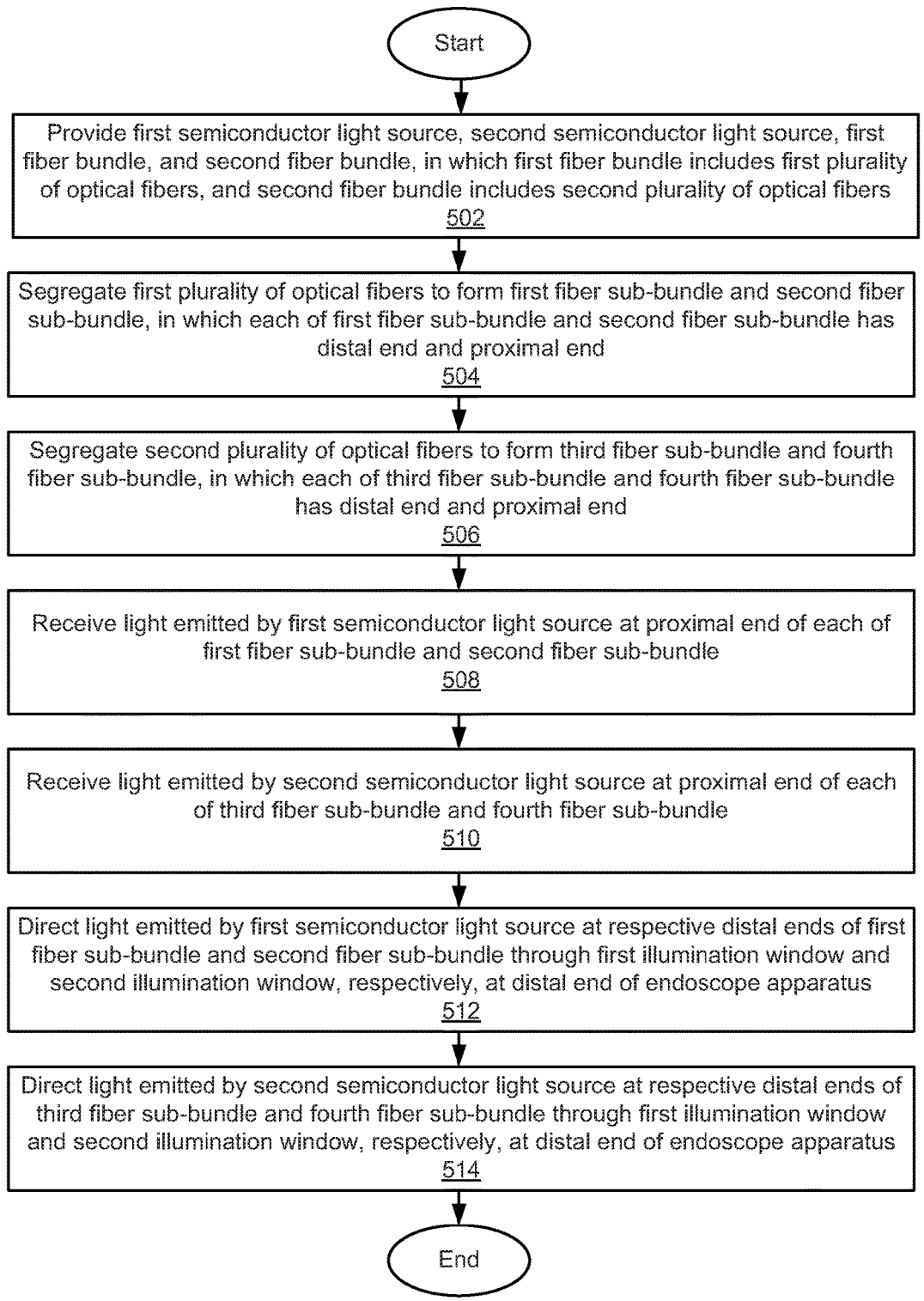
FIG. 5 is a flow diagram of an exemplary method of using the semiconductor-based light source device of FIG. 3 in conjunction with an exemplary endoscope apparatus.

A method of operating the disclosed semiconductor-based light source device for an endoscope apparatus, or any other suitable apparatus, is described herein with reference to FIG. 5. As depicted in block 502, a first semiconductor light source, a second semiconductor light source, a first fiber bundle, and a second fiber bundle are provided, in which the first fiber bundle includes a first plurality of optical fibers, and the second fiber bundle includes a second plurality of optical fibers. As depicted in block 504, the first plurality of optical fibers is segregated to form at least a first fiber sub-bundle and a second fiber sub-bundle, in which each of the first fiber sub-bundle and the second fiber sub-bundle has a distal end and a proximal end. As depicted in block 506, the second plurality of optical fibers is segregated to form at least a third fiber sub-bundle and a fourth fiber sub-bundle, in which each of the third fiber sub-bundle and the fourth fiber sub-bundle has a distal end and a proximal end. As depicted in block 508, light emitted by the first semiconductor light source is received at the proximal end of each of the first fiber sub-bundle and the second fiber sub-bundle. As depicted in block 510, light emitted by the second semiconductor light source is received at the proximal end of each of the third fiber sub-bundle and the fourth fiber sub-bundle. As depicted in block 512, the light emitted by the first semiconductor light source is directed at the respective distal ends of the first fiber sub-bundle and the second fiber sub-bundle through a first illumination window and a second illumination window, respectively, at a distal end of the endoscope apparatus. As depicted in block 514, the light emitted by the second semiconductor light source is directed at the respective distal ends of the third fiber sub-bundle and the fourth fiber sub-bundle through the first illumination window and the second illumination window, respectively, at the distal end of the endoscope apparatus.

It will be appreciated by those skilled in the art that modifications to and variations of the above-described apparatus and methods may be made without departing from the inventive concepts disclosed herein. Accordingly, the invention should not be viewed as limited except as by the scope and spirit of the appended claims.

What is claimed is:
1. An illumination apparatus for use in an endoscope, the endoscope having a distal end, and at least a first illumination window and a second illumination window disposed at the distal end of the endoscope, the illumination apparatus comprising:
    at least a first light source and a second light source; and
    at least a first fiber bundle and a second fiber bundle, the first fiber bundle having a first plurality of optical fibers segregated to form at least a first fiber sub-bundle and a second fiber sub-bundle;
    wherein each of the first fiber sub-bundle, the second fiber sub-bundle, and the second fiber bundle has a distal end and a proximal end,
    wherein the proximal end of each of the first fiber sub-bundle and the second fiber sub-bundle is configured to receive light emitted by at least the first light source,
    wherein the proximal end of the second fiber bundle is configured to receive light emitted by at least the second light source,
    wherein the respective distal ends of the first fiber sub-bundle and the second fiber sub-bundle are configured to direct the light emitted by the first light source to the first illumination window and the second illumination window, respectively, at the distal end of the endoscope,
    wherein the distal end of the second fiber bundle is configured to direct the light emitted by the second light source to the second illumination window at the distal end of the endoscope.

2. The illumination apparatus of claim 1, wherein the first light source is configured to emit light in a first wavelength range, and wherein the second light source is configured to emit light in a second wavelength range different from the first wavelength range.

3. The illumination apparatus of claim 2, wherein the light emitted by the first light source has a first color, and wherein the light emitted by the second light source has a second color different from the first color.

4. The illumination apparatus of claim 2, wherein the light emitted by the first light source is a white light.

5. The illumination apparatus of claim 1, wherein the first fiber sub-bundle and the second fiber sub-bundle each have approximately an equal number of optical fibers.

6. The illumination apparatus of claim 1 further comprising:
    a third light source;
    a third fiber bundle, the third fiber bundle including a third fiber sub-bundle and a fourth fiber sub-bundle;
    wherein the proximal end of each of the third fiber sub-bundle and the fourth fiber sub-bundle is configured to receive light emitted by the third light source, and wherein the respective distal ends of the third fiber sub-bundle and the forth fiber sub-bundle are configured to direct the light emitted by the third light source to the first illumination window and the second illumination window, respectively, at the distal end of the endoscope.

7. The illumination apparatus of claim 6, wherein the first light source is configured to emit light in a first wavelength range, wherein the second light source is configured to emit light in a second wavelength range, and wherein the third light source is configured to emit light in a third wavelength range.

8. The illumination apparatus of claim 7, wherein the light emitted by the first light source has a first color, wherein the light emitted by the second light source has a second color, and wherein the light emitted by the third light source has a third color.

9. The illumination apparatus of claim 8, wherein at least the second light source and the third light source are tunable for adjusting the second color and the third color of light emitted by the second light source and the third light source, respectively.

10. The illumination apparatus of claim 6, further comprising: a plurality of light sources, including the first light source, the second light source, the third light source, and a fourth light source, wherein the first plurality of optical fibers in the first fiber bundle are further segregated to form at least a fifth fiber sub-bundle and an sixth fiber sub-bundle, each of the fifth fiber sub-bundle and the sixth fiber sub-bundle having a distal end and a proximal end, wherein the proximal end of each of the fifth fiber sub-bundle and the sixth fiber sub-bundle is configured to receive light emitted by at least the fourth light source, and wherein the respective distal ends of the fifth fiber sub-bundle and the sixth fiber sub-bundle are configured to direct the light emitted by the fourth light source to the first illumination window and the second illumination window, respectively, at the distal end of the endoscope.

11. The illumination apparatus of claim 10, wherein the fourth light source is configured to emit light in a fourth wavelength range, and at least one of the plurality of light sources is tunable for adjusting a balance of a light output.

12. The illumination apparatus of claim 1, wherein at least one of the first light source and the second light source is a light-emitting diode.

13. The illumination apparatus of claim 1, wherein at least one of the first light source and the second light source is a laser diode.

14. A method of illumination for use in an endoscope, the endoscope having a distal end, and at least a first illumination window and a second illumination window disposed at the distal end of the endoscope, the method comprising:
providing at least a first light source and a second light source;
providing at least a first fiber bundle having a first plurality of optical fibers, and a second fiber bundle having a second plurality of optical fibers;
segregating the first plurality of optical fibers to form at least a first fiber sub-bundle and a second fiber sub-bundle, each of the first fiber sub-bundle and the second fiber sub-bundle having a distal end and a proximal end;
receiving, at the proximal end of each of the first fiber sub-bundle and the second fiber sub-bundle, light emitted by at least the first light source;
receiving, at the proximal end of the second fiber bundle, light emitted by at least the second light source;
directing, at the respective distal ends of the first fiber sub-bundle and the second fiber sub-bundle, the light emitted by the first light source to the first illumination window and the second illumination window, respectively, at the distal end of the endoscope; and
directing, at the distal end of the second fiber bundle, the light emitted by the second light source to the second illumination window at the distal end of the endoscope.

15. The method of claim 14,
wherein the receiving of light emitted by the first light source includes receiving light emitted by the first light source in a first wavelength range, and wherein the receiving of light emitted by the second light source includes receiving light emitted by the second light source in a second wavelength range different from the first wavelength range.

16. An illumination apparatus, comprising:
at least a first light source and a second light source; and
at least a first fiber bundle and a second fiber bundle, the first fiber bundle including at least a first fiber sub-bundle and a second fiber sub-bundle,
wherein a proximal end of each of the first fiber sub-bundle and the second fiber sub-bundle is configured to receive light emitted by at least the first light source,
wherein a proximal end of second fiber bundle is configured to receive light emitted by at least the second light source,
wherein a distal end of the first fiber sub-bundle coupleable to a first illumination window, and
wherein a distal end of each of the second fiber sub-bundle and the second fiber bundle is coupleable to a second illumination window.

17. The illumination apparatus of claim 16, wherein the first light source is configured to emit light in a first wavelength range, and wherein the second light source is configured to emit light in a second wavelength range different from the first wavelength range.

18. The illumination apparatus of claim 16,
wherein the first fiber sub-bundle and the second fiber sub-bundle each have approximately an equal number of optical fibers.

19. The illumination apparatus of claim 16,
wherein at least one of the first light source and the second light source is selected from the group consisting of a light-emitting diode and a laser diode.

* * * * *